United States Patent
Liu et al.

(10) Patent No.: US 9,873,535 B2
(45) Date of Patent: Jan. 23, 2018

(54) MOLYBDATE-FREE STERILIZING AND PASTEURIZING SOLUTIONS

(75) Inventors: Zhendong Liu, Warrington, PA (US); Donald A. Meskers, Jr., Levittown, PA (US); Peter Scheidel, Neckargemuend (DE)

(73) Assignee: Genral Electric Company, Schenectady, NY (US)

( * ) Notice: Subject to any disclaimer, the term of this patent is extended or adjusted under 35 U.S.C. 154(b) by 192 days.

(21) Appl. No.: 14/129,549

(22) PCT Filed: Jun. 19, 2012

(86) PCT No.: PCT/US2012/043068
§ 371 (c)(1),
(2), (4) Date: Mar. 28, 2014

(87) PCT Pub. No.: WO2013/003110
PCT Pub. Date: Jan. 3, 2013

(65) Prior Publication Data
US 2014/0219994 A1 Aug. 7, 2014

Related U.S. Application Data
(60) Provisional application No. 61/502,374, filed on Jun. 29, 2011.

(51) Int. Cl.
| | | |
|---|---|---|
| *B65B 55/02* | (2006.01) | |
| *A01N 37/04* | (2006.01) | |
| *A01N 57/12* | (2006.01) | |
| *C23F 11/12* | (2006.01) | |
| *C23F 11/14* | (2006.01) | |
| *C23F 11/167* | (2006.01) | |
| *B65B 55/10* | (2006.01) | |

(52) U.S. Cl.
CPC .............. *B65B 55/02* (2013.01); *A01N 37/04* (2013.01); *A01N 57/12* (2013.01); *C23F 11/126* (2013.01); *C23F 11/149* (2013.01); *C23F 11/1676* (2013.01); *B65B 55/10* (2013.01)

(58) Field of Classification Search
None
See application file for complete search history.

(56) References Cited

U.S. PATENT DOCUMENTS

| | | | |
|---|---|---|---|
| 2,726,215 A * | 12/1955 | Jones | 252/389.61 |
| 4,284,599 A | 8/1981 | Andersen et al. | |
| 4,303,546 A * | 12/1981 | Waegerle | C02F 5/10 252/180 |
| 4,518,585 A | 5/1985 | Greene et al. | |
| 4,654,374 A | 3/1987 | Martin | |
| 4,689,200 A * | 8/1987 | Cook et al. | 422/15 |
| 4,705,703 A * | 11/1987 | Meier et al. | 427/239 |
| 4,847,017 A * | 7/1989 | Clubley et al. | 562/24 |
| 4,847,304 A | 7/1989 | Bruckner et al. | |
| 4,892,706 A * | 1/1990 | Kralovic | A01N 25/34 204/196.15 |
| 5,116,575 A | 5/1992 | Badertscher et al. | |
| 5,324,477 A | 6/1994 | Schroeder et al. | |
| 5,707,553 A | 1/1998 | Sawyer et al. | |
| 5,900,256 A | 5/1999 | Scoville, Jr. et al. | |
| 6,034,138 A | 3/2000 | Synodis et al. | |

(Continued)

FOREIGN PATENT DOCUMENTS

| | | |
|---|---|---|
| EP | 0451434 | 10/1991 |
| EP | 0544345 | 6/1993 |

(Continued)

OTHER PUBLICATIONS

THWATER entry for "2-hydroxy phosphonoacetic acid" printed 2014; http://www.thwater.net/01-HPAA.htm.*
MeadWestvaco Product Data Bulletin for DIACID 1550 as revised on Dec. 9, 2005; http://www.dealchem.com/Tpl/default/upload/20130530225825472097.pdf.*
Online water hardness calculator of Lenntech.com (http://www.lenntech.com/ro/water-hardness.htm) accessed Jan. 13, 2015.*
Rey et al. "Molybdate and non-molybdate options for closed systems—part II," article presented at 2005 AWT Annual Convention.*
NM & CCo Technical Bulletin for HPA, revised 2003.*

(Continued)

*Primary Examiner* — Ileana Popa
*Assistant Examiner* — Alissa Prosser
(74) *Attorney, Agent, or Firm* — Wegman, Hessler & Vanderburg

(57) ABSTRACT

The present invention concerns a composition and method of using non-molybdate corrosion inhibitors in sterilizing and pasteurizing applications. The composition is a blend of one or more components including corrosion inhibitors, surfactants, hydrotropes, polymer dispersants, pH adjusting agents and water. The composition may include two or more of a) alkyl-dicarboxylic acid; b) phosphono-carboxylic acid; c) tri(amino-carboxylic acid); d) anionic polymer dispersant; e) non-ionic surfactant; f) inorganic phosphate; g) phosphonotricarboxylic acid; and h) hydrotrope. Specifically, the composition may comprise sebacic acid, hydroxyphosphonoacetic acid, and 6,6',6"-(1,3,5-triazine-2,4,6-triyltriimino) tris-hexanoic acid. Optionally, the composition can further comprise a co-polymer of acrylic acid and allyl-2-hydroxy-propyl-sulfonate ether (AA/AHPSE), 2-phosphono-1,2,4-butane-tricarboxylic acid, sodium phosphate monobasic or phosphoric acid, α-decyl-ω-hydroxy-poly(oxy-1,2ethanediyl), and sodium cumenesulfonate. These components are not necessary, and in some embodiments, the composition is utilized without these components. The disclosed composition exhibits comparable or better corrosion protection performance than conventional molybdate containing sterilizing products.

2 Claims, No Drawings

(56) References Cited

U.S. PATENT DOCUMENTS

| | | | |
|---|---|---|---|
| 6,096,348 A | 8/2000 | Miner et al. | |
| 6,310,024 B1 * | 10/2001 | Gill et al. | 510/247 |
| 6,403,028 B1 | 6/2002 | Colby et al. | |
| 6,527,872 B1 | 3/2003 | Fricker et al. | |
| 6,623,695 B2 | 9/2003 | Malchesky et al. | |
| 6,632,397 B1 | 10/2003 | Henderson et al. | |
| 6,866,797 B1 | 3/2005 | Martin et al. | |
| 7,056,536 B2 | 6/2006 | Richter et al. | |
| 7,632,458 B2 * | 12/2009 | Crovetto et al. | 422/15 |
| 2003/0100101 A1 | 5/2003 | Huth et al. | |
| 2006/0270571 A1 | 11/2006 | Burke et al. | |
| 2008/0009549 A1 | 1/2008 | Kawakami et al. | |
| 2009/0061017 A1 | 3/2009 | Pedersen et al. | |
| 2009/0104073 A1 | 4/2009 | Kaiser et al. | |
| 2010/0116473 A1 | 5/2010 | Yang et al. | |
| 2010/0311623 A1 | 12/2010 | Rey et al. | |
| 2011/0052445 A1 | 3/2011 | Herdt et al. | |
| 2011/0160112 A1 * | 6/2011 | Chang et al. | 510/175 |
| 2011/0217204 A1 * | 9/2011 | Franciskovich | A01N 37/16 422/29 |
| 2012/0021963 A1 * | 1/2012 | Kneipp | C23G 1/24 510/259 |
| 2012/0282136 A1 * | 11/2012 | Richardson | C23F 11/18 422/38 |

FOREIGN PATENT DOCUMENTS

| | | | |
|---|---|---|---|
| EP | 1570753 | * 9/2005 | |
| JP | 2004300512 | 10/2004 | |
| WO | WO 9639549 A1 * | 12/1996 | C23F 11/08 |
| WO | 1998/008919 | 3/1998 | |

OTHER PUBLICATIONS

Lenntech Hardness converter calculation, printed 2016; http://www.lenntech.com/calculators/hardness/hardness.htm.*

Aquion "Water hardness," 2015; http://www.aqion.de/site/140.*

PCT International Search Report and Written Opinion for corresponding PCT Application No. PCT/US12/43068, dated Sep. 5, 2012.

* cited by examiner

MOLYBDATE-FREE STERILIZING AND PASTEURIZING SOLUTIONS

BACKGROUND OF THE INVENTION

Field of the Invention

This invention is related to a composition and method of using non-molybdate corrosion inhibitors in sterilizing applications.

Description of Related Art

Food and beverages packaged in cans needs to be sterilized or pasteurized prior to being sold. The food industry normally uses high temperatures to kill microorganisms and preserve the packed food and beverages. Heat preservation of food and beverages covers a range of process water temperatures of 30-150° C. During the sterilization process, food and beverage cans are first heated with hot process water at approximately 120-140° C., and then cooled down by contacting the cans with cooling process water, typically at room temperature. For pasteurization the temperature level is lower with a range of 30-90° C. The cooling process water is often treated with oxidizing biocides such as chlorine and bromine to reduce the risk for re-infection of the cans containing food and beverages. The process water normally has a pH range of 7.5-9.0, and a calcium hardness range of 5-500 ppm as $CaCO_3$, total hardness ranges from 10-800 ppm as $CaCO_3$, m-alkalinity ranges from 5-500 ppm as $CaCO_3$ and chloride ranges from 5-500 ppm. Typically, the water chemistry tends to exhibit lower hardness and lower pH conditions, which makes the water more corrosive. Therefore, the cans and sterilizing equipment need more corrosion protection.

Conventional sterilizing and pasteurizing solutions utilize molybdate, nitrite and zinc as corrosion inhibitors. However, these inhibitors are not environmentally friendly, and have been banned for use in some countries. In addition, molybdate salts are quite expensive. Accordingly, there is a need for a composition that uses non-molybdate corrosion inhibitors for sterilizing and pasteurizing applications and that is more environmental friendly.

The current invention provides for a composition and method of using non-molybdate corrosion inhibitors in sterilizing and pasteurizing applications. Further, the disclosed composition has better performance than the conventional molybdate containing sterilizing products, especially at low hardness, low pH and high chloride conditions and is environmentally friendly.

SUMMARY OF THE INVENTION

The present invention concerns a composition and method of using non-molybdate corrosion inhibitors in sterilizing and pasteurizing applications. The composition is a blend of components including corrosion inhibitors, surfactants, hydrotropes, polymer dispersants, pH adjusting agents and water. The composition may include two or more of a) alkyl-dicarboxylic acid; b) phosphono-carboxylic acid; c) tri(amino-carboxylic acid); d) anionic polymer dispersant; e) non-ionic surfactant; f) inorganic phosphate; g) phosphono-tricarboxylic acid; and h) hydrotrope. Specifically, the composition may comprise sebacic acid, hydroxyphosphono-acetic acid, and 6,6',6"-(1,3,5-triazine-2,4,6-triyltriimino)tris-hexanoic acid. Optionally, the composition can further comprise a co-polymer of acrylic acid and allyl-2-hydroxy-propyl-sulfonate ether (AA/AHPSE), 2-phosphono-1,2,4-butane-tricarboxylic acid, sodium phosphate monobasic or phosphoric acid, α-decyl-ω-hydroxy-poly(oxy-1,2-ethanediyl), and sodium cumenesulfonate. These optional components are not necessary in all applications, and in some embodiments, the composition is utilized without these components. The disclosed composition exhibits better corrosion protection performance than the conventional molybdate containing sterilizing products, especially at low hardness, low pH and high chloride conditions.

The composition is typically prepared in concentrated form and applied to a water stream with a dosage pump. During the sterilization process, food and beverage cans and containers are heated with heating process water to high temperatures, and then cooled down by contacting with cooling process water. For pasteurization the temperature level is lower with a maximum of 90° C. The composition can be introduced in the sterilization or pasteurization process during the heating phase and/or during the cooling phase.

The present invention and its advantages over the prior art will become apparent upon reading the following detailed description and the appended claims.

DETAILED DESCRIPTION OF THE INVENTION

Approximating language, as used herein throughout the specification and claims, may be applied to modify any quantitative representation that could permissibly vary without resulting in a change in the basic function to which it is related. Accordingly, a value modified by a term or terms, such as "about", is not limited to the precise value specified. In at least some instances, the approximating language may correspond to the precision of an instrument for measuring the value. Range limitations may be combined and/or interchanged, and such ranges are identified and include all the sub-ranges stated herein unless context or language indicates otherwise. Other than in the operating examples or where otherwise indicated, all numbers or expressions referring to quantities of ingredients, reaction conditions and the like, used in the specification and the claims, are to be understood as modified in all instances by the term "about".

"Optional" or "optionally" means that the subsequently described event or circumstance may or may not occur, or that the subsequently identified material may or may not be present, and that the description includes instances where the event or circumstance occurs or where the material is present, and instances where the event or circumstance does not occur or the material is not present.

As used herein, the terms "comprises", "comprising", "includes", "including", "has", "having", or any other variation thereof, are intended to cover a non-exclusive inclusion. For example, a process, method, article or apparatus that comprises a list of elements is not necessarily limited to only those elements, but may include other elements not expressly listed or inherent to such process, method, article, or apparatus.

The singular forms "a", "an", and "the" include plural referents unless the context clearly dictates otherwise.

All ranges disclosed in this disclosure are deemed to provide support for any sub-ranges within those ranges and any points within those ranges.

Sterilizing and pasteurizing solutions are used to treat food and beverage cans and containers at high temperatures to kill bacteria, viruses, fungi, yeast and other microorganisms. Sterilization is carried out a higher temperature than pasteurization and is intended to kill all of the unwanted microorganisms, if possible. Pasteurization is carried out at a lower temperature than sterilization and results in the reduction of unwanted microorganism, but not necessarily complete elimination of unwanted microorganisms. During the sterilization process, food and beverage cans and containers are sterilized in a pressurized process vessel, where they are immersed in hot water (otherwise referred to herein as heating process water or process water) or sprayed with hot water. The hot water can be heated by heat exchangers or with steam. The cans and containers are contacted with heating process water at a temperature of 120-140° C. for a desired amount of time to kill bacteria. After the sterilization, the cans and containers are cooled down by contacting with cooling process water, typically at room temperature. For pasteurization, the cans and containers are immersed in hot water or sprayed with hot water at a temperature of less than 90° C., such as 30-90° C., and then are cooled down by contacting with cooling process water, typically at room temperature. The cooling process water is often treated with oxidizing biocides such as chlorine and bromine to reduce the risk for re-infection of the can containing food. Further, the cooling process water typically has a pH range of about 7.5-9, and a calcium hardness range of about 5-500 ppm as $CaCO_3$, a total hardness range from about 10-800 ppm as $CaCO_3$, an m-alkalinity from about 5-500 ppm as $CaCO_3$, and a chloride range from about 5-500 ppm. Typically, the chemistry of the water contains low hardness and low pH conditions, which makes the water more corrosive. Conventional sterilizing and pasteurizing solutions utilize molybdate, nitrite and zinc as corrosion inhibitors. However, these inhibitors are not environmentally friendly and have been banned for use in some countries.

Accordingly, disclosed is a composition and method of using non-molybdate corrosion inhibitors in sterilizing and pasteurizing applications. The composition is a blend of components comprising corrosion inhibitors, surfactants, hydrotropes, polymer dispersants, pH adjusting agents and/or water. Typically, the composition is prepared in concentrated form and then shipped to a customer site. The concentrated solution is then applied to a process water stream with a dosage pump. The process water can be de-ionized water, tap water, or any other suitable type of water as is known in the art without affecting the overall concept of the invention. In the present application, the term "process water" shall mean water that will be or is in contact with the cans and/or containers to heat them up or cool them down, and includes the heating process water and the cooling process water. The term "point-of-use" shall refer to the point at which the process water contacts the cans and/or containers. Once the concentrated composition is added to process water, it becomes diluted. The final effective concentration of active ingredients of the composition in the process water at point-of-use in the sterilizing or pasteurizing equipment is about 5-600 ppm, or more specifically from about 15-400 ppm, or 75-400 ppm. However, other ranges can be used as is known in the art without affecting the overall concept of the invention.

The sterilizing/pasteurizing composition comprises a concentrated amount of a) alkyl-dicarboxylic acid, b) phosphono-carboxylic acid, and optionally c) tri(amino-carboxylic acid). The composition can further comprise an d) anionic polymer dispersant, e) non-ionic surfactant, an f) inorganic phosphate or phosphoric acid, a g) phosphonotricarboxylic acid, and/or h) hydrotrope. These optional components are not necessary in all applications, and in some embodiments, the composition is utilized without these components.

Furthermore, the ranges of the components in the concentrated solution, as active ingredients, can include: a) alkyl-dicarboxylic acid at a range of about 0.2-35% by weight, preferably 0.2-20% by weight, more preferably 0.2-10% by weight and most preferably 0.5-5% by weight, b) phosphono-carboxylic acid at a range of about 0.2-25% by weight, preferably 0.2-15% by weight, more preferably 0.2-10% by weight, and most preferably 0.5-5% by weight, c) tri(amino-carboxylic acid) at a range of about 0-20%, such as 0.1-20% by weight, preferably 0.2-10% by weight, more preferably 0.2-6% by weight, and most preferably 0.5-4% by weight, d) anionic polymer dispersant at a range of about 0-20% by weight, preferably 0.2-15% by weight, more preferably 0.2-10% by weight, and most preferably 0.5-5% by weight, e) non-ionic surfactant at a range of about 0-4% by weight, preferably 0.03-3% by weight, more preferably 0.05-2% by weight, and most preferably 0.1-2% by weight, f) inorganic phosphate or phosphoric acid at a range of about 0-20% by weight, preferably 0.3-15% by weight, more preferably 0.3-10% by weight, and most preferably 0.5-5% by weight, g) phosphonotricarboxylic acid at a range of about 0-25% by weight, preferably 0.2-20% by weight, more preferably 0.2-10% by weight, and most preferably 0.5-5% by weight, and h) hydrotrope at a range of about 0-30% by weight, preferably 0.2-20% by weight, more preferably 0.2-10% by weight, and most preferably 0.5-5% by weight. Furthermore, one or more of potassium hydroxide, sodium hydroxide, ammonia, sulfuric acid, hydrochloric acid, or phosphoric acid can be used to adjust the pH of the composition to a range of about 2-12, preferably a pH range of about 7-12, more preferably a pH range of about 8-11 and most preferably a pH range of about 9-11. The remainder of the composition can be water.

Additionally, the chemical concentration of the composition's active components at point of use in process water (i.e., when contacted with the cans or containers), comprises a) alkyl-dicarboxylic acid at a range of about 0.2-140 ppm, preferably 0.2-80 ppm, more preferably 0.2-40 ppm and most preferably 0.5-20 ppm, b) phosphono-carboxylic acid at a range of about 0.2-100 ppm, preferably 0.2-70 ppm, more preferably 0.2-40 ppm, and most preferably 0.5-20 ppm, c) tri(amino-carboxylic acid) at a range of about 0-80 ppm, such as 0.1-80 ppm, preferably 0.2-40 ppm, more preferably 0.2-24 ppm, and most preferably 0.5-16 ppm, d) anionic polymer dispersant at a range of about 0-80 ppm, preferably 0.2-60 ppm, more preferably 0.2-40 ppm, and most preferably 0.5-20 ppm, e) non-ionic surfactant at a range of about 0-100 ppm, preferably 0.03-20 ppm, more preferably 0.05-10 ppm, and most preferably 0.1-5 ppm, f) inorganic phosphate or phosphoric acid at a range of about 0-80 ppm, preferably 0.2-60 ppm, more preferably 0.2-40 ppm, and most preferably 0.5-20 ppm, g) phosphonotricarboxylic acid at a range of about 0-100 ppm, preferably 0.2-80 ppm, more preferably 0.2-40 ppm, and most preferably 0.5-20 ppm, and/or h) hydrotrope at a range of about 0-120 ppm, preferably 0.2-80 ppm, more preferably 0.2-40 ppm, and most preferably 0.5-20 ppm.

Specifically, the composition, as active ingredients, may comprise one or more of a)-c) (from above) as follows: a) one or more of succinic acid, adipic acid, sebacic acid, azelaic acid, fumaric acid, maleic acid, citraconic acid, itaconic acid, n-dodecenylsuccinic acid, n-dodecylsuccinic acid and their salts thereof, b) one or more of hydroxyphosphonoacetic acid, 2-phosphonobutane-1,2-dicarboxylic acid, methylphosphonosuccinic acid, 1,1-diphosphonopropane-2,3-dicarboxylic acid, 3,3-diphosphono-butane-1,2-dicarboxylic acid and their salts thereof, and e) one or more of 6,6',6"-(1,3,5-triazine-2,4,6-triyltriimino)tris-hexanoic acid, 2,2',2''-(1,4,7-triazanonane-1,4,7-triyl)-triacetic acid, diethylenetriaminepentaacetic acid and their salts thereof.

Optionally, the composition can further comprise one or more of components d)-h) (from above) as follows: d) one or more of polyacrylic acid, polymethacrylic acid, polymaleic acid, polystyrene sulfonic acid, copolymers or terpolymers of acrylic acid, maleic acid, and sulfonic acid or their salts, such as acrylic acid/allyl-2-hydroxy propyl sulfonate ether, (AA/AHPSE), acrylic acid/allylpolyethyleneoxide sulfate ether, (AA/APES), acrylic acid/2-acrylamido-2-methyl-1-propane sulfonic acid, (AA/AMPS), acrylic acid/ammonium allylpolyethoxy sulfate/alloxy-2-hydroxypropane-3-sulfonic acid terpolymer (AA/APES/AHPSE), acrylic acid/methacrylic acid/ammonium allylpolyethyoxy sulfate terpolymers (AA/MA/APES), acrylic acid/2-acrylamido-2-methylpropane sulfonic acid/ammonium allylpolyethoxy sulfate terpolymers (AA/AMPS/APES); e) one or more of ethoxylatedalkylphenols, ethoxylated and propoxylated fatty alcohols, alkylpolyethylene glycol ethers, ethylene oxide-propylene oxide block copolymers, ethylene oxide-butylene oxide block polymers, propylene oxide-butylene oxide block polymers, condensation products of ethylene oxide, propyleneoxide, and butylene oxide with long chain amines or amides, and mixtures thereof. Representative commercial products for e) include Lutensol® XL products (for example Lutensol® XL-80), DOWFAX products (for example DOWFAX 63N10), Tergitol™ products (for example Tergitol™ 15-S-9) and Triton™ products (for example Triton™ X-100). Components f)-h) can be as follows: f) one or more of sodium phosphate monobasic, phosphoric acid, potassium phosphate, sodium phosphate, calcium phosphate, magnesium phosphate, manganese phosphate, nickel phosphate, cobalt phosphate, inorganic polyphosphates and pyrophosphates, such as sodium hexametaphosphate (SHMP), sodium tripolyphosphate (STPP), tetrasodium pyrophosphate (TSPP) and tetrapotassium pyrophosphate (TKPP); g) one or more of 2-phosphono-1,2,4-butanetricarboxylic acid, 1,3,5-tricarboxy pentane-3-phosphonic acid, 1-phosphonopropane-1,2,3-tricarboxylic acid, 1-phosphonobutane-2,3,4-tricarboxylic acid, 3-phosphonobutane-1,2,3-tricarboxylic acid, and their salts thereof; and h) one or more of xylenesulfonic acid and salts, toluenesulfonic acid and salts, cumenesulfonic acid and salts, glycol, glycol ether, monoproprionate and diproprionate. However, components c)-h) are not essential in some applications, and in some embodiments, the composition can be utilized without these components.

Additionally, the process water of the composition typically has a pH range of about 7.5-9.0, a calcium hardness range of about 5-500 ppm as $CaCO_3$, a total hardness range of about 10-800 ppm as $CaCO_3$, m-alkalinity of about 5-500 ppm as $CaCO_3$ and a chloride range of about 5-500 ppm.

In use the concentrated composition is fed into the process water, which dilutes the composition. If the composition is fed to process water which is subsequently heated by steam as opposed to, for example, heat exchangers) prior to sterilization/pasteurization, then the composition is further diluted by the steam upon condensation into water. The amount of the concentrated composition added to the process water is based upon the point-of-use concentration that is desired for the active ingredients. The heating process water is used to sterilize or pasteurize the container, and the cooling process water is used to cool the container. For example, during the sterilization process, food and beverage cans and containers are first heated with heating process water at a temperature of about 120-140° C., and then cooled down by contacting with cooling process water which is typically at room temperature. For pasteurization, the temperature level of the heating process water is lower with a maximum of 90° C., such as 30-90° C. The cooling process water typically has a pH range of about 7.5-9, and a calcium hardness range of about 5-500 ppm as $CaCO_3$, a total hardness range from about 10-800 ppm as $CaCO_3$, an m-alkalinity from about 5-500 ppm as $CaCO_3$, and a chloride range from about 5-500 ppm. Further, the chemistry of the cooling process water contains low hardness and low pH conditions, which makes the water more corrosive for both the containers and the sterilizing/pasteurizing equipment.

Accordingly, the containers are heated with hot process water at a temperature of between 30-150° C., with pasteurizing being between 30-90° C. and sterilizing being between about 120-150° C. Thus, the containers are either sterilized or pasteurized by heating. The heating process water includes the composition, which is often added via the re-circulation line of the sterilizer. In another embodiment, the composition can be present during both the heating phase and the cooling phase by also being added to the process cooling water. When the composition is added to the process water, this is done to prevent corrosion of the containers and/or the sterilizing/pasteurizing equipment.

The present disclosure will now be described more specifically with reference to the following examples. It is to be noted that the following examples are presented herein for purpose of illustration and description; they are not intended to be exhaustive or to limit the disclosure to the precise form disclosed.

Example 1

This example demonstrates that the use of non-molybdate corrosion inhibitors in sterilizing applications exhibits better performance than the conventional molybdate containing sterilizing products, especially at low hardness, low pH and high chloride conditions.

In this test example, a constant temperature water bath is used. The formulations (E1-E4) disclosed in Table 1 are prepared in separate 2 liter beakers and placed in the water bath, Lutensol XL-80 contains α-decyl-ω-hydroxy-poly(oxy-1,2ethanediyl), Eltesol SC40 contains sodium cumenesulfonate, Bayhibit AM contains 2-phosphono-1,2,4-butane-tricarboxylic acid, Belcor 575 contains hydroxyphosphonoacetic acid, Belcor 593 contains 6,6',6''-(1,3,5-triazine-2,4,6-triyltriimino)tris-hexanoic acid, and DCA 222 contains allyl-2-hydroxy-propyl-sulfonate ether (AA/AHPSE), with the remaining balance of the formulations E1-E4 being de-ionized water. Once the formulations E1-E4 are prepared, potassium hydroxide or sulfuric acid is then used to adjust the pH. Each of the formulations E1-E4 has a pH of 7.5, a 25 ppm calcium hardness as $CaCO_3$, 40 ppm total hardness as $CaCO_3$, 25 ppm m-alkalinity, and 200 ppm chloride. The beakers containing formulations E1-E4 are then placed in the water bath and kept at a constant temperature of 80° C. for 18 hours.

Low carbon steel (LCS) electrodes are then placed in the beakers and the electrochemical corrosion rates of the electrodes are monitored by an electrochemical instrument for approximately 18 hours. In addition, LCS coupons are also placed in the beakers to measure the corrosion rate by weight loss. The test results are shown in Table 2.

TABLE 1

Experimental Formulations

| Formulations | Lutensol XL-80, ppm | Eltesol SC40, ppm | Bayhibit AM, ppm | Belcor 575, ppm | Belcor 593, ppm | DCA 222, ppm | Sodium phosphate monobasic, ppm | Sebacic acid, ppm |
|---|---|---|---|---|---|---|---|---|
| E1 | 1.5 | 4.2 | 8.5 | 18 | 26 | 10 | 10 | |
| E2 | 1.5 | 4.2 | 8.5 | 18 | 26 | 10 | 10 | 40 |
| E3 | 1.5 | 4.2 | 8.5 | 18 | 13 | 10 | 10 | 20 |
| E4 | 1.5 | 4.2 | 8.5 | 9 | 6.5 | 10 | 10 | 10 |

TABLE 2

Test Results

| Treatment Solutions | pH | Corrosion rate by weight loss, mg/year | Corrosion rate by electrochemical monitoring, MPY |
|---|---|---|---|
| E1 | 7.5 | 9.73 | 2.84 |
| E2 | 7.5 | 3.00 | 0.74 |
| E3 | 7.5 | 3.87 | 0.75 |
| E4 | 7.5 | 3.73 | 1.47 |
| 300 ppm Baseline Product A (including 41 ppm Molybdate) | 7.5 | 13.67 | 8.78 |
| 300 ppm Baseline Product B (including 15 ppm Molybdate) | 7.5 | 5.07 | 1.70 |

As can be seen, the test results show that the use of non-molybdate corrosion inhibitors in sterilizing applications exhibits comparable or better performance than the conventional molybdate containing sterilizing products at lower hardness, lower pH and higher chloride conditions.

Example 2

In this test example, a constant temperature water bath is used. The formulations (E5-E6) disclosed in Table 3 are prepared in separate 2 liter beakers and placed in the water bath. For example, Lutensol XL-80 includes α-decyl-ω-hydroxy-poly(oxy-1,2ethanediyl), Eltesol SC40 includes sodium cumenesulfonate, Bayhibit AM includes 2-phosphono-1,2,4-butane-tricarboxylic acid, Belcor 575 includes hydroxyphosphonoacetic acid, Belcor 593 includes 6,6',6"-(1,3,5-triazine-2,4,6-triyltriimino)tris-hexanoic acid, and DCA 222 includes allyl-2-hydroxy-propyl-sulfonate ether (AA/AHPSE), with the remaining balance of the formulations E5-E6 being de-ionized water. Once the formulations E5-E6 are prepared, potassium hydroxide or sulfuric acid is then used to adjust the pH. Each of the formulations E5-E6 has a pH of either 7.5 or 8.8, a 200 ppm calcium hardness as $CaCO_3$, 320 ppm total hardness as $CaCO_3$, 100 ppm m-alkalinity, and 200 ppm chloride. The beakers containing formulations E5-E6 are then placed in the water bath and kept at a constant temperature of 80° C. for 18 hours.

Low carbon steel (LCS) electrodes are then placed in the beakers and the electrochemical corrosion rates of the electrodes are monitored by an electrochemical instrument for approximately 18 hours. In addition, LCS coupons are also placed in the beakers to measure the corrosion rate by weight loss. The test results are shown in Table 4,

TABLE 3

Experimental Formulations

| Formulations | Lutensol XL-80, ppm | Eltesol SC40, ppm | Bayhibit AM, ppm | Belcor 575, ppm | Belcor 593, ppm | DCA 222, ppm | Sodium phosphate monobasic, ppm | Sebacic acid, ppm |
|---|---|---|---|---|---|---|---|---|
| E5 | 0.75 | 2.1 | 4.25 | 4.5 | 3.25 | 5 | 5 | 5 |
| E6 | 0.75 | 2.1 | 4.25 | 4.5 | 3.25 | 5 | 3 | 5 |

TABLE 4

Test Results

| Treatment Solutions | pH | Corrosion rate by weight loss, mg/year | Corrosion rate by electrochemical monitoring, MPY |
|---|---|---|---|
| E5 | 8.8 | 8.00 | 1.72 |
| E6 | 7.5 | 2.87 | 1.37 |
| E6 | 8.8 | 4.73 | 1.19 |
| 150 ppm Baseline Product B (containing 7.5 ppm Molybdate) | 7.5 | 7.07 | 1.42 |
| 150 ppm Baseline Product B (containing 7.5 ppm Molybdate) | 8.8 | 9.47 | 2.48 |

As can be seen, the test results show that the use of non-molybdate corrosion inhibitors in sterilizing applications exhibits comparable or better performance than the conventional molybdate containing sterilizing products at higher hardness and higher chloride conditions.

While this invention has been described in conjunction with the specific embodiments described above, it is evident that many alternatives, combinations, modifications and variations are apparent to those skilled in the art. Accordingly, the preferred embodiments of this invention, as set forth above are intended to be illustrative only, and not in a limiting sense. Various changes can be made without departing from the spirit and scope of this invention. Therefore, the technical scope of the present invention encompasses not only those embodiments described above, but also all that fall within the scope of the appended claims.

This written description uses examples to disclose the invention, including the best mode, and also to enable any person skilled in the art to practice the invention, including making and using any devices or systems and performing any incorporated processes. The patentable scope of the invention is defined by the claims, and may include other examples that occur to those skilled in the art. These other examples are intended to be within the scope of the claims if they have structural elements that do not differ from the literal language of the claims, or if they include equivalent structural elements with insubstantial differences from the literal language of the claims.

What is claimed is:

1. A method of sterilizing or pasteurizing a container, comprising contacting the container with a process water solution comprising:
   a) an alkyl-dicarboxylic acid,
   b) a phosphono-carboxylic acid,
   c) tri(amino-carboxylic acid),
   d) anionic polymer dispersant,
   e) non-ionic surfactant,
   f) inorganic phosphate,
   g) phosphonotricarboxylic acid, and
   h) hydrotope,
wherein said process water solution is at a temperature of about 30-150° C. and
wherein said a) alkyl-dicarboxylic acid is a member selected from the group consisting of succinic acid, adipic acid, sebacic acid, azelaic acid, fumaric acid, maleic acid, citraconic acid, itaconic acid, n-dodecenylsuccinic acid, and n-dodecylsuccinic acid and salts thereof, b) is hydroxyphosphonoacetic acid, c) is 6,6',6" (1,3,5-triazine-2,4,6-triyltriimino)tris hexanoic acid, d) is acrylic acid/allyl-2-hydroxy propyl sulfonate ether (AA/AHPSE), e) is α-decyl-ω-hydroxy-poly(oxy-1,2 ethanediyl), f) is monobasic $NaPO_4$, and h) is sodium cumene sulfonate.

2. The method as recited in claim 1 wherein a) is sebacic acid.

* * * * *

UNITED STATES PATENT AND TRADEMARK OFFICE
CERTIFICATE OF CORRECTION

PATENT NO. : 9,873,535 B2
APPLICATION NO. : 14/129549
DATED : January 23, 2018
INVENTOR(S) : Zhendong Liu, Donald A. Meskers, Jr. and Peter Scheidel It is certified that error appears in the above-identified patent and that said Letters Patent is hereby corrected as shown below:

On the Title Page

(73) Assignee:, delete "Genral Electric Company" and insert -- General Electric Company --

Signed and Sealed this
Seventeenth Day of April, 2018

Andrei Iancu
*Director of the United States Patent and Trademark Office*